Figure 1A:
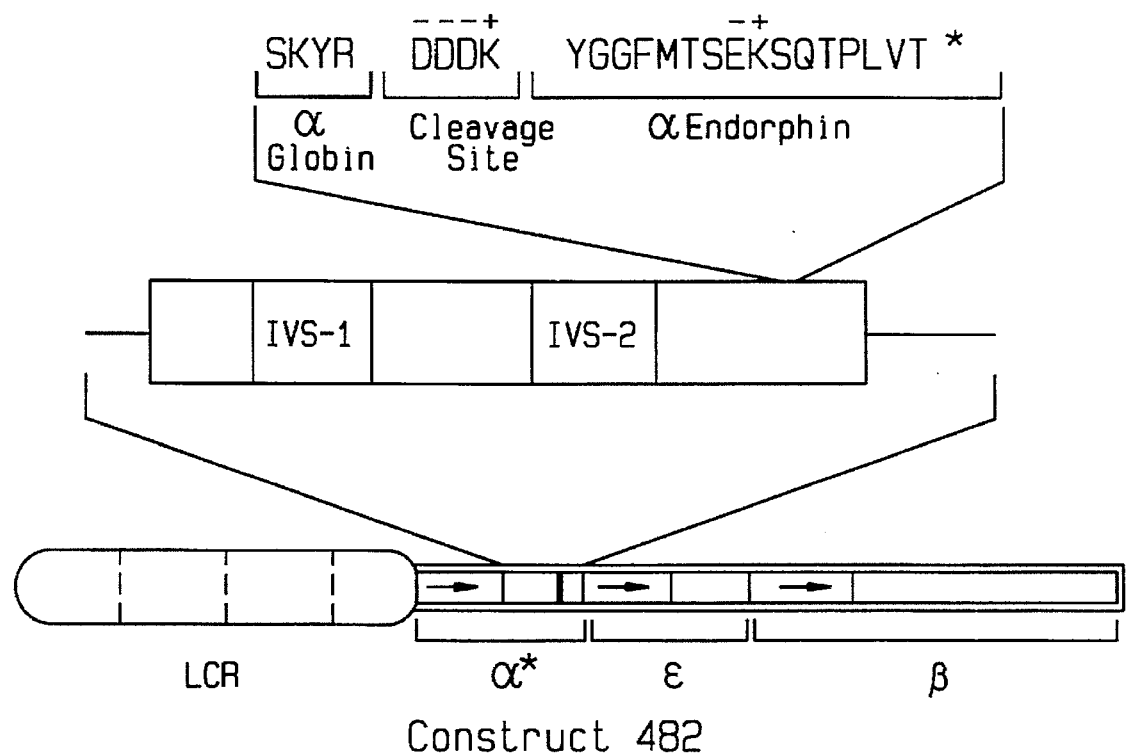

United States Patent [19]

Kumar et al.

[11] Patent Number: 5,627,268

[45] Date of Patent: May 6, 1997

[54] HEMOGLOBIN COMPRISING GLOBIN FUSION PROTEINS

[75] Inventors: Ramesh Kumar, Pennington; Ajay Sharma, Laurenceville, both of N.J.; Anastasia M. Khoury-Christianson, Philadelphia, Pa.

[73] Assignee: DNX BioTherapeutics, Princeton, N.J.

[21] Appl. No.: 255,272

[22] Filed: Jun. 7, 1994

[51] Int. Cl.$^6$ .................. C07K 14/805; C07K 14/815; C07K 14/585; C12P 21/06

[52] U.S. Cl. .................. 530/385; 530/300; 530/302; 530/307; 530/315; 435/69.7

[58] Field of Search .................. 530/385, 380, 530/381, 300, 302, 307, 315; 435/69.7

[56] References Cited

U.S. PATENT DOCUMENTS 4,873,191  10/1989  Wagner .................. 435/172.3

FOREIGN PATENT DOCUMENTS

| | | |
|---|---|---|
| WO89/01517 | 2/1989 | WIPO . |
| WO92/11380 | 7/1992 | WIPO . |
| WO92/22644 | 12/1992 | WIPO . |
| WO93/04171 | 3/1993 | WIPO . |
| WO93/25567 | 12/1993 | WIPO . |
| WO94/05796 | 3/1994 | WIPO . |
| WO95/04744 | 2/1995 | WIPO . |

OTHER PUBLICATIONS

Booth et al., 1988, "The Use of a 'universal' yeast expression vector to produce an antigenic protein of *Mycobacterium leprae*", *Immunol. Lett.* 19: 65.

Diessenroth and Hendrick, 1978, "Human α–Globin Gene Expression Following Chromosomal Dependent Gene Transfer into Mouse Erythroleukemia Cells", *Cell* 15: 55.

Dykes et al., 1988, "Expression of atrial natriuretic factor as a cleavable fusion protein with chloramphenicol acetyltransferase in *Escherichia coli*", *Eur. J. Biochem.* 174: 411.

Gordon et al., 1980, "Genetic transformation of mouse embryos by microinjection of purified DNA", *Proc. Natl. Acad. Sci. USA* 77: 7380–7384.

Gordon et al., 1989, Transgenic Animals, *Intl. Rev. Cytol.* 115: 171–229.

Gordon and Ruddle, 1981, "Integration and Stable Germ Line Transmission of Genes Injected into Mouse Pronuclei", *Science* 214: 1244–1246.

Gordon and Ruddle, 1983, "Gene Transfer into Mouse Embryos: Production of Transgenic Mice by Pronuclear Injection", *Recombinant DNA Part C, Methods in Enzymol.* 101: 411–433.

Wright et al., 1983, "Regulated expression in the human β–globin gene family in murine erythroleukaemia cells", *Nature* 305: 333.

Hanscombe et al., 1989, "High–level, erythroid–specific expression of the human α–Globin gene in transgenic mice and the production of human hemoglobin in murine erythrocytes", *Genes Dev.* 3: 1572.

(List continued on next page.)

*Primary Examiner*—Robert A. Wax
*Assistant Examiner*—K. Cochrane Carlson
*Attorney, Agent, or Firm*—Pennie & Edmonds

[57] ABSTRACT

The present invention relates to a novel method for making a predetermined, desired peptide in transgenic animals and can be advantageously used for the production of large quantities of the desired peptide. More particularly, the invention concerns the engineering of a transgenic animal having an artificial gene, which is controlled by globin locus control region (LCR) and which encodes a fusion protein, in which the desired peptide is joined via a cleavable peptide linker to a globin polypeptide. The erythrocytes of the transgenic animal express the fusion globin which is incorporated into hemoglobin produced by the host cell. The desired peptide can be obtained from a hemolysate of the red cells of the transgenic animals by enzymatic or chemical cleavage at the linker.

11 Claims, 11 Drawing Sheets

OTHER PUBLICATIONS

Hardison and Miller, 1993, "Use of Long Sequence Alignments to Study the Evolution and Regulation of Mammalian Globin Gene Clusters", *Mol. Biol. Evol.* 10: 73–107.

Lavitrano et al., 1989, "Sperm Cells as Vectors for Introducing Foreign DNA into Eggs:Genetic Transformation of Mice", *Cell* 57: 717–723.

Li et al., 1991, "Primary Structure of the Goat β–Globin Locus Control Region" *Genomics* 9: 488.

Li et al., 1990, "β–GLobin locus activation regions: Conservation of organization, structure and function", *Proc. Natl. Acad. Sci.* 87: 8207.

Li et al., 1985, "Nucleotide Sequence of 16–Kilobase Pairs of DNA 5' to the Human ε–Globin Gene", *J. Biol. Chem.* 260: 14901.

Lo, 1983, "Transformation by Iontophoretic Microinjection of DNA: Multiple Integrations Without Tandem Insertions", *Mol. Cell. Biol.* 3: 1803–1814.

Margot et al., 1989, "Complete Nucleotide Sequence of the Rabbit β–like Globin Gene Cluster" *J. Mol. Biol.* 205: 15–40.

Parks et al., 1994, "Release of Proteins and Peptides from Fusion Proteins Using a Recombinant Plant Virus Proteinase" *Analytical Biochemistry* 216: 413.

Prysiecki et al., 1992, "Characterization of Recombinant Antistasin Secreted by *Saccharomyces cerevisiae*", *Protein Expr. Purif.* 3: 185.

Schellenberger et al., 1988, "Peptide production by a combination of gene expression, chemical synthesis, and protease–catalyzed conversion" *Int. J. Pept. Protein Res.* 41: 326.

Shehee, et al., 1989, "Nucleotide Sequence of the BALB/c Mouse β–Globin Complex" *J. Mol. Biol.* 205: 41.

Swanson et al., 1992, "Production of functional human hemoglobin in transgenic swine", *Biotechnology* 10: 557.

Thompson et al., 1989, "Germ Line Transmission and Expression of a Corrected HPRT Gene Produced by Gene Targeting in Embryonic Stem Cells", *Cell* 56: 313–321.

Van Assendelft et al., 1989, "The β–Globin Dominant Control Region Activates Homologous and Heterologous Promoters in a Tissue–Specific Manner", *Cell* 56: 969.

Van Der Putten, 1985, "Efficient insertion of genes into the mouse germ line via retroviral vectors", *Proc. Natl. Acad. Sci. USA* 82:6148–1652.

Wilmut, et al., 1991, "Production of pharmaceutical proteins in milk", *Experientia* 47: 905.

FIG. 2C1
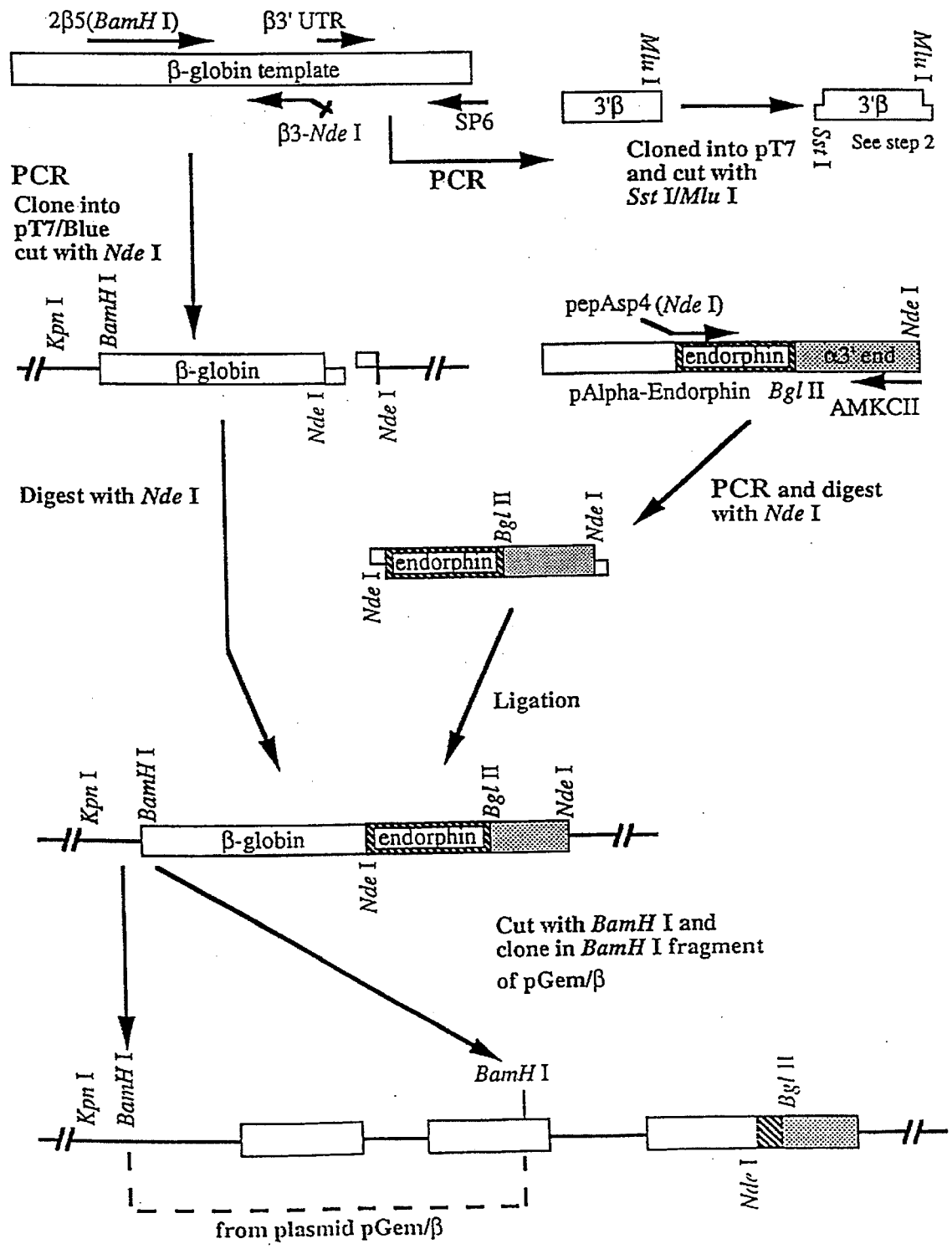

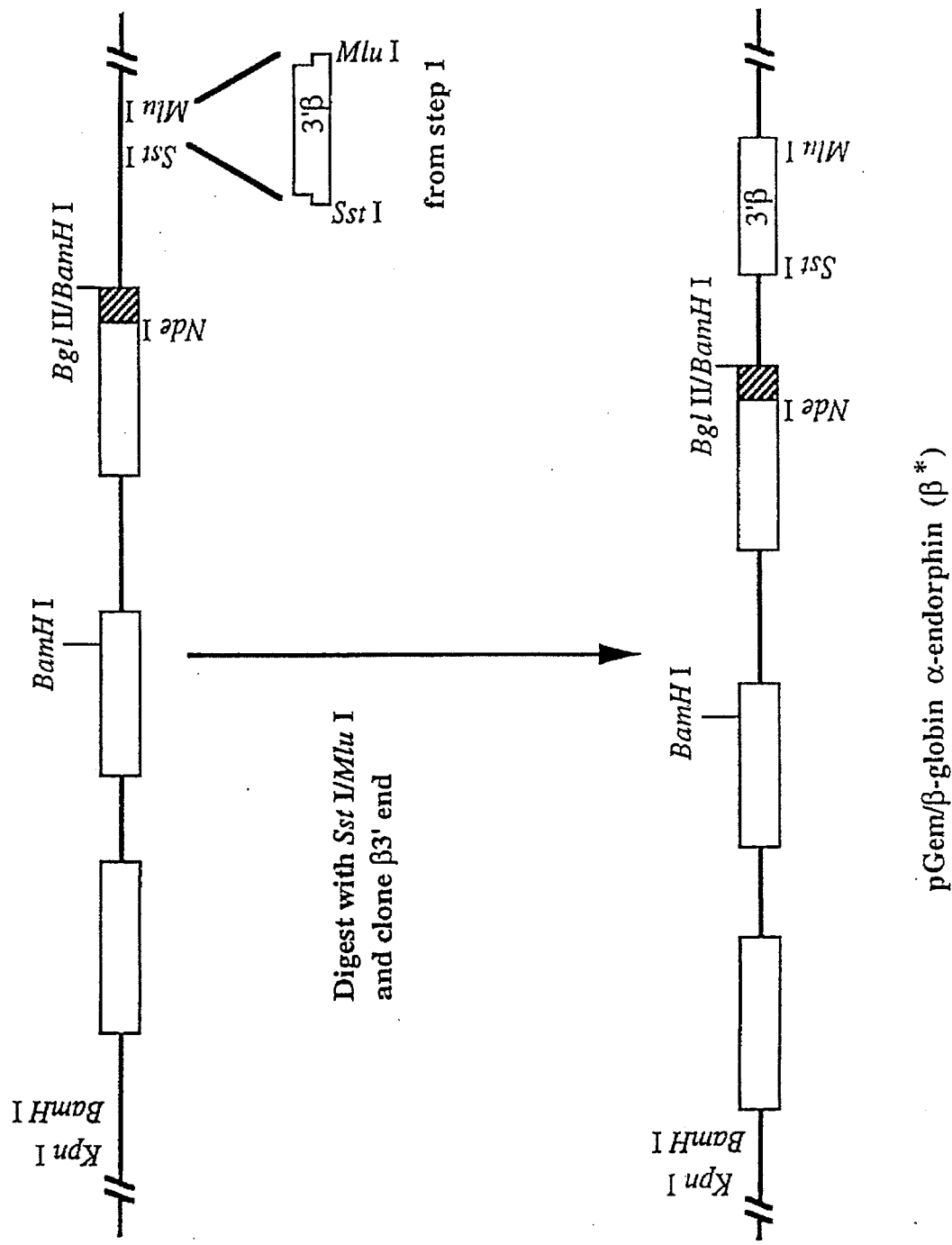
FIG. 2C2

FIG. 3A

Primers Used to Make α-Globin-D₃K-α-Endorphin

| Primer | Orientation | Name | Sequence |
|---|---|---|---|
| I | sense | 5H3A-Hind III | TG CAC GCG CAC AAG CTT CGG GTG GAC CCG G |
| II | antisense | α-endoI-Bgl II | GAG AGT CGA CAG ATC TTA GGT CAC CAG GGG GGT CTG GCT CTT CTC |
| III | sense | AMKCI-Bgl II | GCC AGA TCT GCT GGA GCC TCG |
| IV | antisense | SP6 | ATTTAGGTGACACTAGAGAAT C |

Primers Used to Make α-globin-LVPR D₄K-Magainin

| Primer | Orientation | Name | Sequence |
|---|---|---|---|
| I | (sense) | 5H3A-Hind III | as above |
| II | (antisense) | Hα3'-SacII | GCC AAC CAG GCC GCG GTA TTT GGA GGT CAG CAC GGT |
| INSERT | (sense) | | ACC TCC AAA TAC CGC GGC CTG GTT CCC CGG GGC ATA GGC AAG TTC CTG CAC TCC GCC AAA AAG TTT GGT AAG GCT TTC GTG GGC GAG ATA ATG AAC TCC TAA GTC GAC AGA TCT GCT GGA GCC |
| III | (sense) | AMKC1-Bgl II | as above |
| IV | (antisense) | SP6 | as above |

FIG. 3B

Primers Used to Make β-globin LMD₅K-endorphin

| | | | |
|---|---|---|---|
| I | sense | 2β5-BamH1 | GT<u>G GAT CCT</u> GAG AAC TTC AG |
| II | antisense | β3-NdeI | GTC CAT ATG ATA CTT GTG GGC |
| III | sense | pep D₄-NdeI | TAT CAT ATG GAT (GAC)₄ AAG TAC |
| IV | antisense | AMKC1 | as above |
| V | sense | β3UTR | GTC CGC TTT CTT G |
| VI | Antisense | Sp6 | as above |

SEQUENCE LISTING ( 1 ) GENERAL INFORMATION:

( i i i ) NUMBER OF SEQUENCES: 32

( 2 ) INFORMATION FOR SEQ ID NO:1:

( i ) SEQUENCE CHARACTERISTICS:
( A ) LENGTH: 10 amino acids (B) TYPE: amino acid
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:1:

Pro Glu Trp Pro Arg Pro Gln Ile Pro Pro
1               5                   10

(2) INFORMATION FOR SEQ ID NO:2:

(i) SEQUENCE CHARACTERISTICS:
    (A) LENGTH: 9 amino acids
    (B) TYPE: amino acid
    (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:2:

Arg Pro Pro Gly Phe Ser Pro Phe Arg
1               5

(2) INFORMATION FOR SEQ ID NO:3:

(i) SEQUENCE CHARACTERISTICS:
    (A) LENGTH: 16 amino acids
    (B) TYPE: amino acid
    (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:3:

Tyr Gly Gly Phe Met Thr Ser Glu Lys Ser Gln Thr Pro Leu Val Thr
1               5                   10                  15

(2) INFORMATION FOR SEQ ID NO:4:

(i) SEQUENCE CHARACTERISTICS:
    (A) LENGTH: 14 amino acids
    (B) TYPE: amino acid
    (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:4:

Pro Glu Leu Tyr Glu Asn Lys Pro Arg Arg Pro Tyr Ile Leu
1               5                   10

(2) INFORMATION FOR SEQ ID NO:5:

(i) SEQUENCE CHARACTERISTICS:
    (A) LENGTH: 14 amino acids
    (B) TYPE: amino acid
    (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:5:

```
Ala Gly Cys Lys Asn Phe Phe Trp Lys Thr Phe Thr Ser Cys
1               5                   10
```

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:6:

```
Arg Pro Lys Pro Gln Gln Phe Phe Gly Leu Met
1               5                   10
```

(2) INFORMATION FOR SEQ ID NO:7:

(i) SEQUENCE CHARACTERISTICS:
        (A) LENGTH: 31 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:7:

```
His Asn Lys Gln Gln Gly Arg Asp His Asp Lys Ser Lys Gly His Phe
1               5                   10                  15
His Arg Val Val Ile His His Lys Gly Gly Leu Ala His Arg Gly
            20              25                  30
```

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:8:

```
Leu Cys Thr Cys Cys Ala
1               5
```

(2) INFORMATION FOR SEQ ID NO:9:

(i) SEQUENCE CHARACTERISTICS:
        (A) LENGTH: 23 amino acids
        (B) TYPE: amino acid
        (D) TOPOLOGY: unknown (ii) MOLECULE TYPE: peptide ( i i i ) HYPOTHETICAL: NO ( i v ) ANTI-SENSE: NO ( x i ) SEQUENCE DESCRIPTION: SEQ ID NO:9:

```
Gly Ile Gly Lys Phe Leu His Ser Ala Lys Lys Phe Gly Lys Ala Phe
1               5                   10                  15

Val Gly Glu Ile Met Asn Ser
                20
```

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

```
Val Pro Asp Pro Arg
1               5
```

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

```
Lys Cys Thr Cys Cys Ala
1               5
```

( 2 ) INFORMATION FOR SEQ ID NO:12:

( i ) SEQUENCE CHARACTERISTICS:
        ( A ) LENGTH: 22 amino acids
        ( B ) TYPE: amino acid
        ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

```
Ile Lys Cys Asn Cys Lys Arg His Val Ile Lys Pro His Ile Cys Arg
1               5                   10                  15

Lys Ile Cys Gly Lys Asn
                20
```

( 2 ) INFORMATION FOR SEQ ID NO:13:

( i ) SEQUENCE CHARACTERISTICS:
        ( A ) LENGTH: 9 amino acids
        ( B ) TYPE: amino acid
        ( D ) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:13:

Met Gln Met Lys Lys Val Leu Asp Ser
1               5

(2) INFORMATION FOR SEQ ID NO:14:

(i) SEQUENCE CHARACTERISTICS:
        (A) LENGTH: 9 amino acids
        (B) TYPE: amino acid
        (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:14:

Val Gln Gly Glu Glu Ser Asn Asp Lys
1               5

(2) INFORMATION FOR SEQ ID NO:15:

(i) SEQUENCE CHARACTERISTICS:
        (A) LENGTH: 21 amino acids
        (B) TYPE: amino acid
        (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:15:

Cys Ser Cys Ser Ser Leu Met Asp Lys Glu Cys Val Tyr Phe Cys His
1               5                   10                  15

Leu Asp Ile Ile Trp
            20

(2) INFORMATION FOR SEQ ID NO:16:

(i) SEQUENCE CHARACTERISTICS:
        (A) LENGTH: 32 amino acids
        (B) TYPE: amino acid
        (D) TOPOLOGY: unknown (i i) MOLECULE TYPE: peptide (i i i) HYPOTHETICAL: NO (i v) ANTI-SENSE: NO (x i) SEQUENCE DESCRIPTION: SEQ ID NO:16:

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
                20                  25                  30

(2) INFORMATION FOR SEQ ID NO:17:

(i) SEQUENCE CHARACTERISTICS:
        (A) LENGTH: 65 amino acids
        (B) TYPE: amino acid ( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:17:

```
Val Val Tyr Thr Asp Cys Thr Glu Ser Gly Gln Asn Leu Cys Leu Cys
1               5                   10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
            35                  40                  45

Gln Ser His Asn Asp Gly Asp Phe Glu Glu Ile Pro Glu Glu Tyr Leu
            50                  55                  60

Gln
65
```

( 2 ) INFORMATION FOR SEQ ID NO:18:

( i ) SEQUENCE CHARACTERISTICS:
( A ) LENGTH: 9 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( x i ) SEQUENCE DESCRIPTION: SEQ ID NO:18:

```
Cys Tyr Ile Gln Asn Cys Pro Leu Gly
1               5
```

( 2 ) INFORMATION FOR SEQ ID NO:19:

( i ) SEQUENCE CHARACTERISTICS:
( A ) LENGTH: 5 amino acids
( B ) TYPE: amino acid
( D ) TOPOLOGY: unknown ( i i ) MOLECULE TYPE: peptide ( i i i ) HYPOTHETICAL: NO ( i v ) ANTI-SENSE: NO ( i x ) FEATURE:
( A ) NAME/KEY: Region
( B ) LOCATION: 1
( D ) OTHER INFORMATION: /label= X
/ note= "X can be no residue or D"

( x i ) SEQUENCE DESCRIPTION: SEQ ID NO:19:

```
Xaa Asp Asp Asp Lys
1               5
```

( 2 ) INFORMATION FOR SEQ ID NO:20:

( i ) SEQUENCE CHARACTERISTICS:
( A ) LENGTH: 4 amino acids
( B ) TYPE: amino acid
( D ) TOPOLOGY: unknown ( i i ) MOLECULE TYPE: peptide ( i i i ) HYPOTHETICAL: NO (iv) ANTI-SENSE: NO (xi) SEQUENCE DESCRIPTION: SEQ ID NO:20:

Ile Glu Gly Arg
1

(2) INFORMATION FOR SEQ ID NO:21:

(i) SEQUENCE CHARACTERISTICS:
(A) LENGTH: 4 amino acids
(B) TYPE: amino acid
(D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO:21:

Leu Val Pro Arg
1

(2) INFORMATION FOR SEQ ID NO:22:

(i) SEQUENCE CHARACTERISTICS:
(A) LENGTH: 4 amino acids
(B) TYPE: amino acid
(D) TOPOLOGY: unknown (ii) MOLECULE TYPE: peptide (iii) HYPOTHETICAL: NO (iv) ANTI-SENSE: NO (v) FRAGMENT TYPE: C-terminal (xi) SEQUENCE DESCRIPTION: SEQ ID NO:22:

Ser Lys Tyr Arg
1

(2) INFORMATION FOR SEQ ID NO:23:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (iii) HYPOTHETICAL: NO (xi) SEQUENCE DESCRIPTION: SEQ ID NO:23:

TGCACGCGCA CAAGCTTCGG GTGGACCCGG 30

(2) INFORMATION FOR SEQ ID NO:24:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (iii) HYPOTHETICAL: NO (xi) SEQUENCE DESCRIPTION: SEQ ID NO:24:

```
GAGAGTCGAC   AGATCTTAGG   TCACCAGGGG   GGTCTGGCTC   TTCTC                                45
```

( 2 ) INFORMATION FOR SEQ ID NO:25:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:25:

```
GCCAGATCTG   CTGGAGCCTC   G                                                              21
```

( 2 ) INFORMATION FOR SEQ ID NO:26:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:26:

```
ATTTAGGTGA   CACTAGAGAA   TC                                                             22
```

( 2 ) INFORMATION FOR SEQ ID NO:27:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( x i ) SEQUENCE DESCRIPTION: SEQ ID NO:27:

```
GCCAACCAGG   CCGCGGTATT   TGGAGGTCAG   CACGGT                                            36
```

( 2 ) INFORMATION FOR SEQ ID NO:28:

( i ) SEQUENCE CHARACTERISTICS:
        ( A ) LENGTH: 123 base pairs
        ( B ) TYPE: nucleic acid
        ( C ) STRANDEDNESS: double
        ( D ) TOPOLOGY: linear ( i i ) MOLECULE TYPE: DNA ( i i i ) HYPOTHETICAL: NO ( x i ) SEQUENCE DESCRIPTION: SEQ ID NO:28:

```
ACCTCCAAAT   ACCGCGGCCT   GGTTCCCCGG   GGCATAGGCA   AGTTCCTGCA   CTCCGCCAAA              60

AAGTTTGGTA   AGGCTTTCGT   GGGCGAGATA   ATGAACTCCT   AAGTCGACAG   ATCTGCTGGA              120

GCC                                                                                      123
```

( 2 ) INFORMATION FOR SEQ ID NO:29:

( i ) SEQUENCE CHARACTERISTICS:
        ( A ) LENGTH: 20 base pairs
        ( B ) TYPE: nucleic acid

```
            ( C ) STRANDEDNESS: single
            ( D ) TOPOLOGY: linear ( i i ) MOLECULE TYPE: DNA ( i i i ) HYPOTHETICAL: NO ( x i ) SEQUENCE DESCRIPTION: SEQ ID NO:29:

GTGGATCCTG AGAACTTCAG                                                      20

( 2 ) INFORMATION FOR SEQ ID NO:30:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( x i ) SEQUENCE DESCRIPTION: SEQ ID NO:30:

GTCCATATGA TACTTGTGGG C                                                    21

( 2 ) INFORMATION FOR SEQ ID NO:31:

( i ) SEQUENCE CHARACTERISTICS:
            ( A ) LENGTH: 30 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( x i ) SEQUENCE DESCRIPTION: SEQ ID NO:31:

TATCATATGG ATGACGACGA CGACAAGTAC                                           30

( 2 ) INFORMATION FOR SEQ ID NO:32:

( i ) SEQUENCE CHARACTERISTICS:
            ( A ) LENGTH: 13 base pairs
            ( B ) TYPE: nucleic acid
            ( C ) STRANDEDNESS: single
            ( D ) TOPOLOGY: linear ( i i ) MOLECULE TYPE: DNA ( i i i ) HYPOTHETICAL: NO ( x i ) SEQUENCE DESCRIPTION: SEQ ID NO:32:

GTCCGCTTTC TTG                                                             13
```

HEMOGLOBIN COMPRISING GLOBIN FUSION PROTEINS

1. INTRODUCTION

The present invention relates to a novel method for making a desired peptide in transgenic animals. Once engineered, the transgenic animals can be economically propagated by the traditional techniques of animal husbandry. Thus, the present invention can be advantageously used for the production of large quantities of the desired peptide.

More particularly, the engineering of a transgenic animal having an artificial gene, which is controlled by globin locus control region (LCR) and which encodes a fusion protein is described. In the fusion protein, the desired peptide is linked via a cleavable peptide bond to a globin polypeptide. The erythrocytes of the transgenic animal express the fusion protein which is incorporated into hemoglobin produced by the host cell. The desired peptide can be obtained from a hemolysate of the red cells of the transgenic animals by cleavage of the linking bond and separation of the peptide away from globin portions. The invention further involves the design of a peptide containing the cleavable bond so that the fusion protein is incorporated into hemoglobin.

2. BACKGROUND

Techniques presently available for the synthesis of peptides are not satisfactory for synthesizing peptides of between about 4 and 140 amino acids in length in high purity and at low unit cost.

2.1 CHEMICAL MEANS OF PEPTIDE SYNTHESIS

There are well known chemical techniques to manufacture peptides, most frequently by attaching the nascent peptide to a solid phase resin. The techniques of solid phase peptide synthesis can conveniently be used to make small quantities of peptides. Substantial disadvantages occur when more than milligram quantities of product are desired. These include the high cost of starting materials and the generation of large quantities of toxic chemical waste, the disposal of which is both hazardous and expensive. In addition, the initial product of solid phase peptide synthesis is a highly heterogeneous mixture, in which the desired peptide of interest may be a minor component. The necessity for the large scale purification of the peptide of interest from this heterogeneous mixture further adds to the cost of production. As the length of the peptide of interest increases, so do the difficulties and expense associated with the isolation of the peptide of interest from the initial product mixture. Thus, the production of large quantities of even moderately sized peptides is costly.

2.2 BIOLOGICAL METHODS TO OBTAIN A PEPTIDE PRODUCT

There are several well known techniques for the production of a desired protein by means of recombinant DNA technology. These include systems based on the well-known E.coli-based recombinant DNA technology, for examples of which, see infra., wherein the use of these techniques to produce peptides is described. The shortcomings of E. coli based systems include instability, insolubility and occasionally toxicity to the host of the product. More specialized systems have been developed to produce large quantities of a product efficiently in transiently infected eukaryotic cells. Most successful of these expression systems based on the baculovirus infected, cultured insect cells have produced foreign proteins in quantities of up to only about 1 gram per liter of culture wherein the protein of interest comprises between about 25% and 50% of the total protein. BACULOVIRUS EXPRESSION VECTORS/A Laboratory Manual by D. R. O'Reilly, L. K. Miller & V. A. Luckow (W. R. Freeman & Co.). With suitable modifications the baculovirus system can be used to produce recombinant proteins in insect larva.

The foregoing systems are poorly suited to the production of large amounts of very small proteins, i.e., of peptides. Peptides, which do not have a compact tertiary structure tend to be unstable in living cells. Conformationally non-compact peptides may be engineered with larger stable proteins, to form fusion proteins. However, the use of such a fusion protein carrier would further reduce the total yield necessitating still larger scales of production at still larger expense.

Efforts to synthesize peptides by biological means have involved engineering fusion proteins which consist of a support protein and a peptide of interest linked by a peptide sequence which is cleavable by a sequence specific enzyme. The fusion protein is then expressed in either a bacterial or a yeast host, isolated, cleaved and the peptide of interest is then recovered.

Examples of such a fusion protein approach in E.coli include Schellenberger, V. et al., 1988, INT.J.PEPT.PROTEIN RES. 41: 326 (production of Substance P); Dykes et al., 1988, EUR.J.BIOCHEM 174: 411 (production of human natriuretic factor 1–28); and Parks, et al., 1994, ANALYTICAL BIOCHEMISTRY 216: 413 (production of several proteins and a 34 residue peptide). Separation of the peptide or protein of interest and the support protein is accomplished by enterokinase, thrombin, trypsin, tobacco etch virus protease, or skatole. A major difficulty with this approach is the necessity of physically or enzymatically disrupting the bacteria by a technique, involving precipitation and centrifugation, which is labor intensive and therefore unsuited for large scale production.

To overcome this disadvantage, other workers have constructed a fusion protein wherein the leader sequence of a yeast mating factor, which is normally secreted by the yeast, is fused to the product of interest and causes it to be secreted into the culture medium. Cleavage of the leader and the product of interest can be accomplished by either constitutive yeast enzymes, Prysiecki, C.T., et al., 1992, PROTEIN EXPR.PURIF. 3: 185, or by an exogenous enzyme, e.g., enterokinase, Booth, R. J. et al., 1988, IMMUNOL. LETT. 19: 65. Such techniques, however, yield only comparatively low concentrations of product. Prysiecki reports recovery of only about 1 mg of product per liter of culture media.

In view of the foregoing, there is a need for a method whereby large quantities of peptide product can be readily produced.

2.3 THE EXPRESSION OF PROTEINS IN TRANSGENIC ANIMALS

There have been suggestions to use transgenic animals to produce proteins of one species in another. In one approach the transgenic animal is engineered to produce the foreign protein in the milk. One application of this technology is the production of infant formula, which would contain human rather than bovine proteins. DeBoer, H. A., et al., 1993, WO93/25567; Bergstrom, S., et al., 1993, WO93/04171. However, the same technology can be employed to produce proteins not normally found in milk. Drohan, W., et al., 1994, WO94/05796; Devinoy, E., et al., 1992 WO92/22644; Wilmut, I., et al., 1991, EXPERIENTIA 47: 905 .

In a different approach, the α- and β-globin genes from one animal species can be introduced into the germ line of another species so that the foreign α-globin is expressed at nearly physiologic levels in the mature red blood cells of the transgenic host. Hanscombe O., et al., 1989, GENES DEV. 3: 1572; Swanson, M. E. et al., 1992, BIOTECHNOLOGY 10: 557. However, transgenic animals have not heretofore been engineered to produce peptides.

3. SUMMARY OF THE INVENTION

The invention relates to a method of production of peptides having a specifically desired sequence and to the protein and nucleic acid intermediates necessary for the practice of the method. The sequence to be produced can be identical to the desired end product (the peptide of interest) or it can contain one or more tandem copies of the peptide of interest and additionally it can contain sequences associated with a selectively cleavable bond through which the peptide is covalently attached to a globin polypeptide. The method of the invention comprises the steps of:

a) providing a gene which encodes a fusion protein having a globin polypeptide and a peptide product linked through a selectively cleavable peptide bond, which gene is operably connected to a globin locus control region and a globin promoter, the fusion protein can also contain a peptide linker;

b) making a transgenic animal having the operably connected fusion gene integrated into its genome, whereby the fusion protein is expressed and incorporated into the hemoglobin of the erythrocytes of the transgenic animal;

c) isolating the erythrocytes from the blood of transgenic animal and obtaining a hemolysate which is substantially free (<5% contamination) of non-hemoglobin proteins when particular high levels of purity are desired;

d) cleaving the selectively cleavable peptide bond, so that the peptide of interest remains intact and a predetermined peptide is freed from the globin containing polypeptides; and e) isolating the predetermined peptide from the globin polypeptides.

A means to predict whether the peptide/globin fusion protein will be incorporated into hemoglobin in the transgenic animal is important to the method of the invention. The present invention is based, in part, on the discovery that control of the electric charge of the fusion protein is critical to obtaining its incorporation into hemoglobin. According to the teaching of the invention, the charge of the fusion protein for any particular peptide of interest can be controlled by engineering the charge of the linker so that the net charge of the linker and peptide of interest does not prevent its incorporation into hemoglobin. Preferably, the net charge lies between −6 and +4. The peptide and linker should also preferably be smaller than the globin polypeptide and more preferably smaller than about 65 amino acids and most preferably smaller than about 30 amino acids for maximal incorporation into hemoglobin.

In an alternative embodiment of the present invention, an erythroleukemia cell line can be transfected in place of the construction of transgenic animals. The transfected cell line can then be induced to undergo in vitro erythroid differentiation so that the fusion protein is synthesized and, if stable, incorporated into hemoglobin. This embodiment is useful to verify that the gene encoding the fusion protein is functional prior to the construction of the transgenic animal and to determine the level at which the fusion protein will be stably incorporated into hemoglobin. By these means, several alternative linkers can be tested to determine which linker is best suited to produce a particular peptide of interest.

The method of the invention employs to advantage the fact that greater than 95% of the soluble protein of normal erythrocytes (red blood cells) is hemoglobin which is present in amounts of up to 15 grams per 100 milliliters of blood. In the preferred embodiment of the invention the linker is cleaved so that the hemoglobin protein tetramer does not disassociate. However, even under condition where the hemoglobin disassociates into the globin monomer the peptide of interest can then be readily separated from the globin fraction by a method which the ordinary practitioner will readily determine after consideration of the structure of the peptide of interest. Such methods include ion exchange chromatography, RP-HPLC (Reverse Phase High Pressure Liquid Chromatography) precipitation and molecular filtration.

3.1 DEFINITIONS

As used herein, the following single letter amino acid code is employed:

| A | Ala | M | Met |
|---|-----|---|-----|
| C | Cys | N | Asn |
| D | Asp | P | Pro |
| E | Glu | Q | Gln |
| F | Phe | R | Arg |
| G | Gly | S | Ser |
| H | His | T | Thr |
| I | Ile | V | Val |
| K | Lys | W | Trp |
| L | Leu | Y | Tyr. |

4. BRIEF DESCRIPTION OF THE FIGURES

FIG. 1A. Nucleic acids of the invention encoding an α-endorphin-α-globin and magainin-α-globin fusion proteins. The peptide sequences were fused to the C terminus of human α globin. A 4- or 5-amino acid bridge region, the cleavage site for endoprotease Enterokinase, was introduced between the globin and the endorphin sequences. The position of introns (IVS-1 and -2) and the fused peptide sequence (black bar) are shown. The complete expression vectors were assembled from human μβLCR, human ε and β genes and the fusion α gene.

Figure 1B:
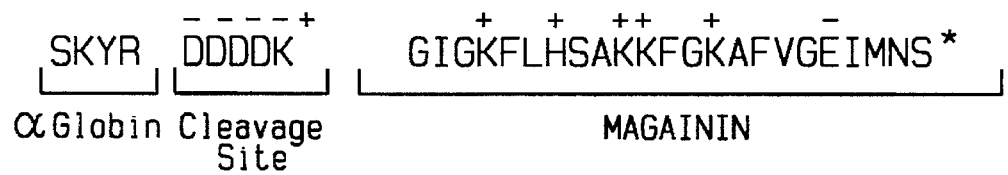

FIG. 1B. The amino acid sequence of the last 4 residues of α-globin, a linker and magainin.

FIGS. 2A, 2B, 2C and 2D. Schematic description of the construction of genes encoding a globin/peptide-of-interest fusion protein: A) the construction of α-globin-DDDK-α-endorphin; B) the construction of α-globin-LVPR-magainin; C) the construction of β-globin-DDDDDK-α-endorphin from the β-globin gene and (A); and D) the replacement of the LVPR linker of (B) by DDDDK.

FIG. 3. The sequence of the oligonucleotide primers and inserts which were used to construct genes encoding the globin/peptide of interest fusion proteins.

Figure 4A:
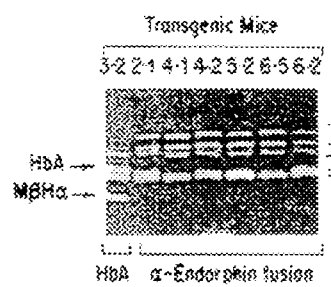
Figure 4B:
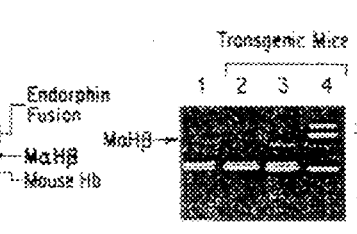
Figure 4C:
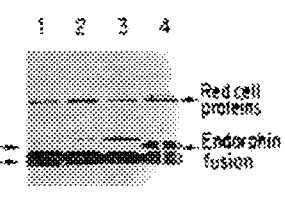

FIG. 4A, 4B AND 4C. The expression of fusion proteins in transgenic mice. Iso-electric focussing gel electrophoresis was employed to detect hemoglobin in the hemolysate of transgenic mice. FIG. 4A. First generation (G0) mice. The first lane displays a hemoglobin pattern obtained for a mouse (3-2) carrying construct 339 designed to express human hemoglobin. The migration of human, murine and two inter-species hybrids are indicated. The other 6 lanes display hemoglobin patterns of transgenic mice carrying the α-globin-α-endorphin fusion expression vector. FIG. 4B. Production of a magainin fusion protein. Iso-electric focussing analysis of hemolysates prepared from transgenic mice. The migration of various types of hemoglobin dimers is shown. Lane 1, non-transgenic mouse, lanes 2 and 3, transgenic mice containing the magainin expression vector 560. Lane 4, transgenic mouse expressing endorphin fusion hemoglobin. FIG. 4C. An SDS-PAGE indicating the migration of α and β globin chains and the fusion globin chains is shown. The position of the endorphin and magainin fusion proteins and other red cell proteins.

Figure 5:
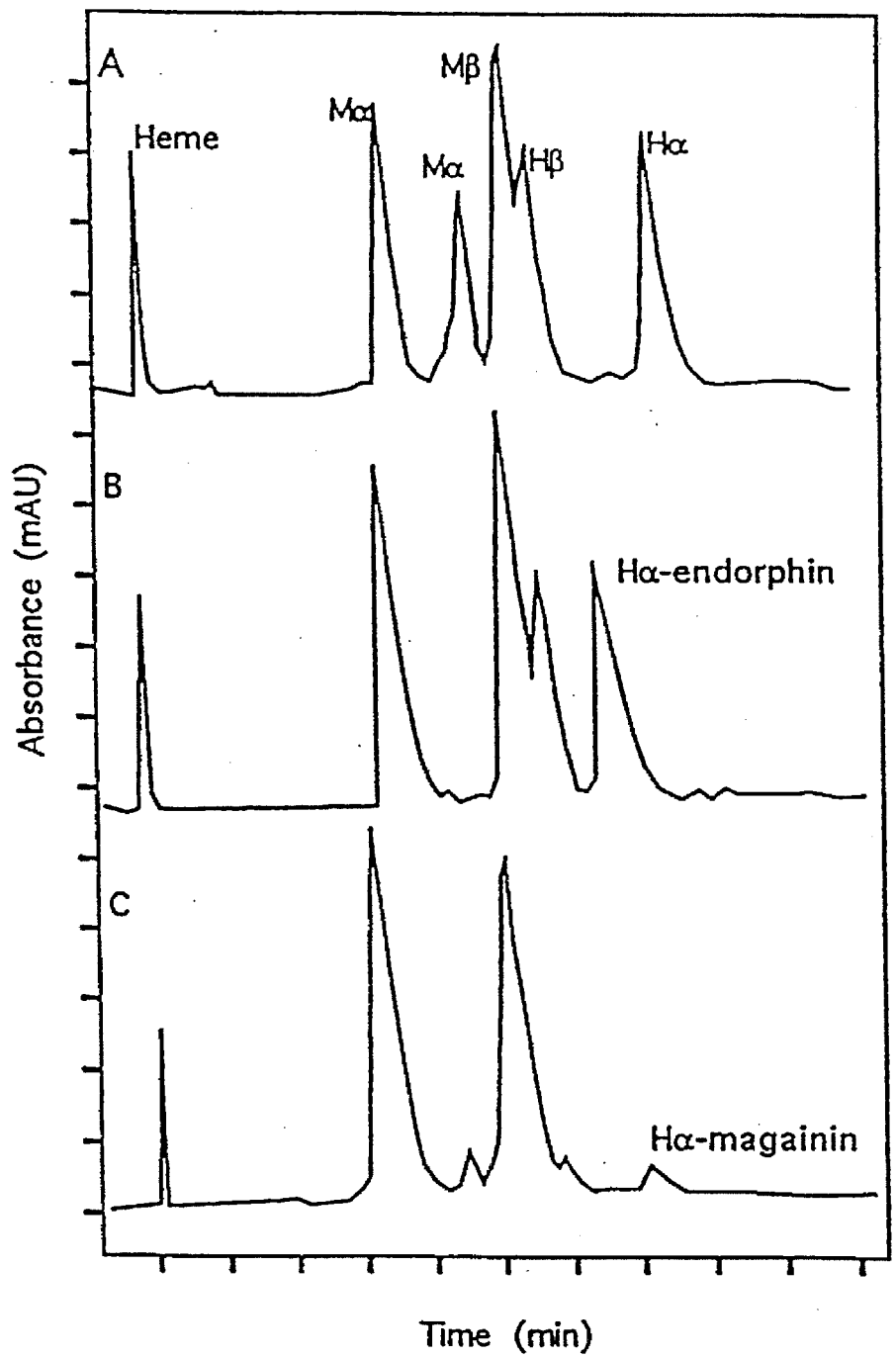

FIG. 5. Reverse Phase HPLC analysis of normal and fusion hemoglobin. Approximately 150 µg of crude hemolysate was fractionated on a C4 column. Fractions were monitored spectrophotometrically at 210 nm. TRACE A: Transgenic hemolysate containing HbA. TRACE B: Hemolysate containing the endorphin fusion. TRACE C: Hemolysate containing the magainin fusion. The position of peaks corresponding to human and murine globin chains and to the fusion e globin chain (α*) are indicated.

Figure 6:
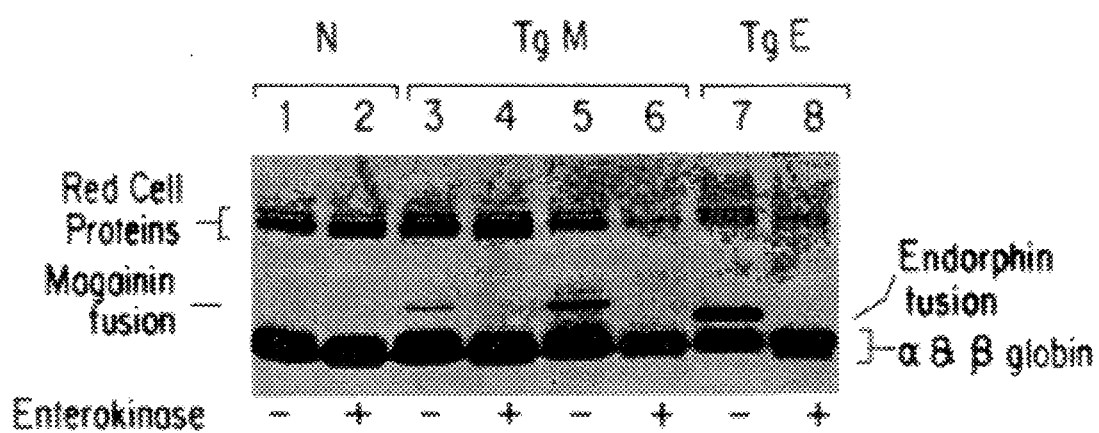

FIG. 6. Enterokinase digestion. Hemolysates prepared from blood samples of non-transgenic (N) and transgenic mice expressing magainin or endorphin fusion proteins (Tg M and Tg E, respectively) were incubated with enterokinase for 16 h at 25C. Samples taken before (−) or after (+) digestion were resolved by SDS-PAGE. The position of magainin fusion- (lanes 3 and 5) and endorphin fusion-(lane 7) α globins, the non-globin red cell proteins (seen in all lanes) and the α and β globins (seen in all lanes) are indicated.

5. DETAILED DESCRIPTION OF THE INVENTION

The present invention provides for a method of producing a desired peptide of interest. It further provides for vectors designed to direct the expression of fusion proteins that are useful intermediates for the production of the desired peptides.

The fusion protein of the invention is composed of a globin polypeptide and a peptide product which are linked by a peptide bond, which can be cleaved selectively, by, for example, an enzyme, so that a peptide is separated from the globin. In one embodiment, there is an additional element, a linker, with which the selectively cleavable peptide bond is associated. For example, the linker can allow for the selective cleavage by an enzyme. The products of cleavage of the linker can include a globin having none, some or all of the residues of the linker attached and the desired peptide having none, some or all of the residues of the linker attached. Hereinafter the term "redetermined peptide" will be used to refer to either the desired peptide or the desired peptide and the portion of the linker remaining attached thereto after cleavage.

In an embodiment, the peptide portion of the fusion protein contains several copies of the peptide of interest which are connected by selectively cleavable peptide bonds so that for each copy of the fusion protein contains multiple copies of the peptide of interest. As used herein the term desired peptide includes a peptide having one copy of the peptide of interest or multiple copies linked by selectively cleavable bonds.

When expressed in erythroid cells the fusion protein of the invention is incorporated into a hemoglobin molecule. Each hemoglobin molecule consists of two dimers. The dimers are formed by the association of an α- and a β-globin. Thereafter, two αβ dimers associate to form a hemoglobin. When a single fusion gene is constructed, then each hemoglobin can contain at most two fusion proteins and many hemoglobins in erythroid cells of the transgenic will contain one or no fusion proteins. When the fusion gene is constructed using both an α and a β globin gene then hemoglobins having between zero and four fusion proteins can be produced.

Nucleotide sequences which encode the fusion proteins of the invention can be prepared and cloned in cloning vectors that can be used to propagate the coding sequence. Expression vectors include a regulatory element that directs expression of the fusion protein coding sequence in host cells, preferably erythroid cells. In a preferred embodiment, a globin locus control region (LCR) and a globin promoter are operably linked to a gene encoding the fusion protein of the invention.

In one embodiment of the invention, the coding sequence for the fusion protein is engineered in a polynucleotide having a cluster of globin genes, each under the control of the LCR. In an alternate embodiment, the nucleic acid consists of an LCR and a promoter operably linked to a single copy of the coding sequence a fusion protein. In a preferred embodiment the promoter and the globin gene are isologous with the host. In an alternate preferred embodiment, the promoter and the globin gene are the human α and β globin gene and promoter.

The developmental and tissue specific regulation of globin expression can be accomplished through a locus control region (LCR). In a preferred embodiment the LCR is the µβLCR of Grosveld, F. G., 1989, WO 89/01517 and 1992, WO 92/11380.

Transgenic animals can be engineered containing the fusion protein coding sequence as the transgenes incorporated into its genome.

The invention also includes erythroleukemia cells which contain the coding sequence for the fusion protein operatively associated with a regulatory element that directs expression of the coding sequence in the erythroleukemic host cell.

5.1 CONSTRUCTION OF CODING SEQUENCES FOR THE FUSION PROTEIN

Any peptide can be engineered using the fusion protein approach of the invention. Examples of desirable peptides are shown in Table 1 below.

TABLE 1

| Therapeutic Peptides | | |
|---|---|---|
| Peptide | Sequence | Activity |
| ACE Inhibitor | PEWP RPQI PP (SEQ. ID NO: 1) | Cardiovascular |
| Bradykinin | RPPG FSPF R (SEQ. ID NO: 2) | Cardiovascular |
| α Endorphin | YGGF MTSE KSQT PLVT (SEQ. ID NO: 3) | Analgesic |
| Neurotensin | PELY ENKP RRPY IL (SEQ. ID NO: 4) | Neurobiological |
| Somatostatin | AGCK NFFW KTFT SC (SEQ. ID NO: 5) | Growth |
| Substance P | RPKP QQFF GLM (SEQ. ID NO: 6) | Gastric |
| Inhibin like | HNKQ QGRD HDKS | Reproduction |

TABLE 1-continued

Therapeutic Peptides

| Peptide | Sequence | Activity |
| --- | --- | --- |
| | KGHF HRVV IHHK GGLA HRG (SEQ. ID NO: 7) | |
| Metallothionein | LCTC CA (SEQ. ID NO: 8) | Detoxification |
| Magainin | GIGK FLHS AKKF GKAF VGEI MNS (SEQ. ID NO: 9) | Anti-infective |
| Appetite Inhibitor | VPDP R (SEQ. ID NO: 10) | Dietary |
| Metallothionein | KCTC CA (SEQ. ID NO: 11) | Detoxification |
| Degranulation | IKCN CKRH VIKP HICR KICG KN (SEQ. ID NO: 12) | Neurotoxic |
| Anti Inflamm. | MQMK KVLD S (SEQ. ID NO: 13) | Immune |
| IL-1β Fragment | VQGE ESND K (SEQ. ID NO: 14) | T cell activation |
| Endothelin I | CSCS SLMD KECV YFCH LDII W (SEQ. ID NO: 15) | Cardiovascular |
| Calcitonin | CGNL STCM LGTY TQDF NKFH TFPQ TAIG VGAP (SEQ. ID NO: 16) | Bone Calcification |
| Hirudin | See SEQ. ID NO: 17 | Anti-coagulant |
| Oxytocin | CYIQ NCPL G (SEQ. ID NO: 18) | Lactation |

A suitable linker must be selected for each peptide so that its cleavage will not result in the destruction of the peptide of interest. Examples of suitable linkers are shown below.

TABLE 2

Representative Linkers for Fusion Proteins

| Reagent | Linker |
| --- | --- |
| Cyanogen Bromide | M |
| Hydroxylamine | NG |
| Enterokinase | DDDDK/DDDK/DK/EK (SEQ. ID NO: 19) |
| Factor Xa | IEGR (SEQ. ID NO: 20) |
| Thrombin | LVPR (SEQ. ID NO: 21) |

For example, enterokinase, which is most active in cleaving the sequence xxDDDDKxx SEQ ID NO. 19 also shows activity at analogous sequences such as xxEKxx and should be avoided whenever the peptide of interest contains the EK dipeptide.

The linker should be selected so as not to unduely disturb the net electric charge of the globin fusion protein. Otherwise, the fusion protein is not successfully assembled into a tetrameric hemoglobin. Thus, when the globin is an α-globin, the peptide product and linker collectively should preferably have a net charge of between −4 and +4 inclusive preferably +2, +1 or 0; when the globin is a β-globin the net charge on the peptide product and linker collectively should be between −6 and +2 inclusive preferably −2, −1 or 0. The linker sequence can be chosen to counteract the net charge of the desired peptide. The electrostatic charge of the desired peptide and linker can be adjusted by the addition of charged residues between the globin and the cleavage site of the linker. For example, the number of negative carboxyl functions in a enterokinase linker can be adjusted by varying the number of aspartyl residues from 1 upwards.

The preferred embodiment of the invention contemplates having only a single copy of the peptide of interest joined to a globin polypeptide. The invention contemplates that several copies of the desired peptide, linked by a short cleavable sequence, e.g., a methionine, can be present in the fusion protein. The combination of linker and predetermined peptide of interest can be up to about 140 amino acids, preferably, less than about 65 and most preferably less than about 30.

A gene encoding a globin-linker-peptide can be constructed by a combination of means known to those skilled in the art starting from a plasmid containing a globin gene. Typical means include oligonucleotide synthesis, particularly, solid phase oligonucleotide synthesis, and in vitro enzymatic DNA synthesis, particularly, polymerase chain reaction (PCR) DNA synthesis, and recombinant DNA techniques. By way of non-limiting example two strategies are outlined below. The implementation of these strategies utilizes a plasmid containing the an α-globin or a β-globin gene and an expression vector suitable for use in erythroid cells.

Figure 2A:
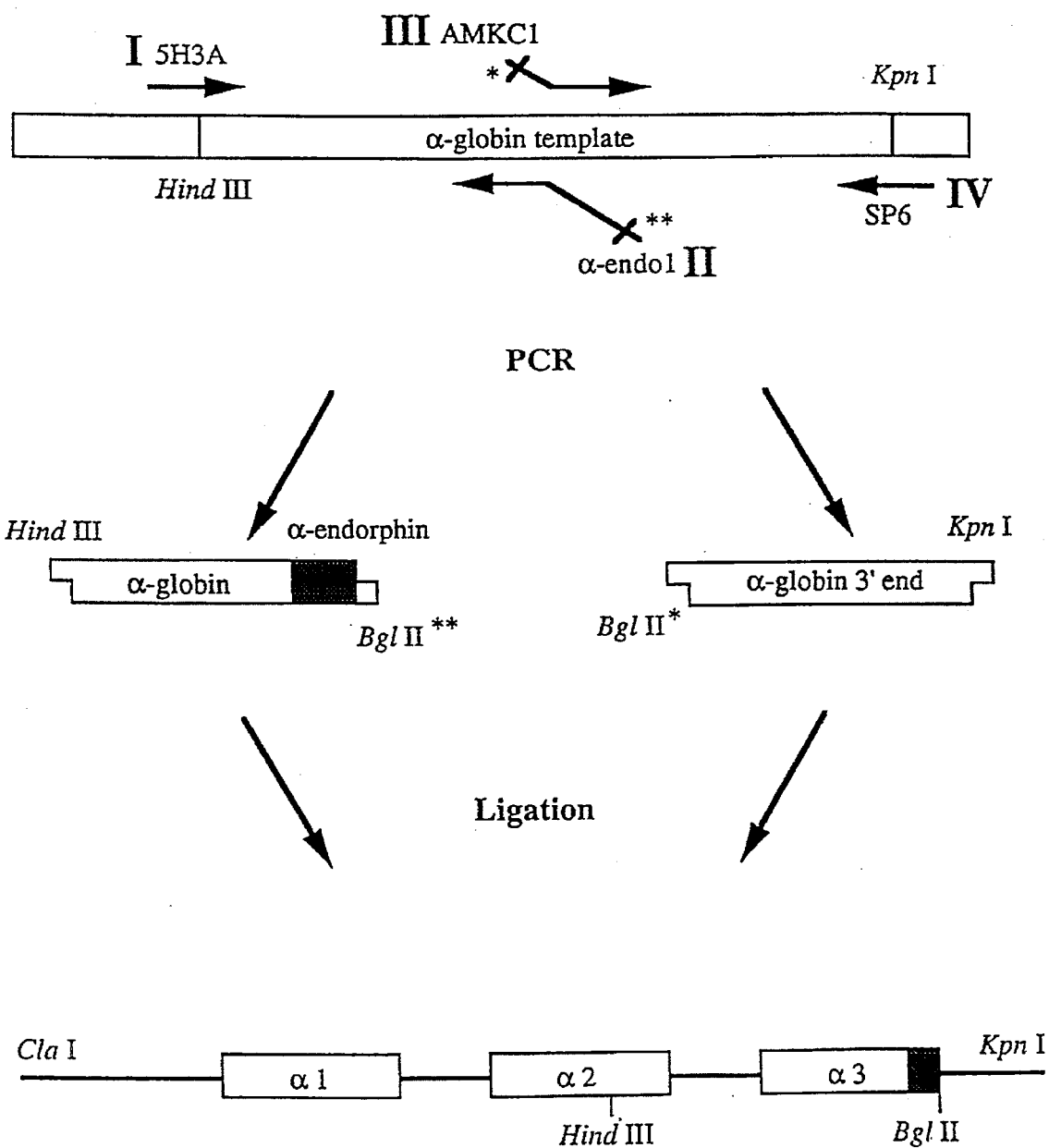

The first exemplary strategy, which is the preferred strategy for the synthesis of smaller peptides of interest, is schematically illustrated in FIG. 2A. Four oligonucleotide primers are synthesized for use in PCR. A Primer I is selected to contain a unique restriction enzyme site within a globin gene and is complementary to the antisense strand of the gene. A Primer I for human α-globin is 5H3A-Hind III of FIG. 3 (SEQ ID NO: 23), which contains a Hind III site. A Primer I for human β-globin 2β3-Bam HI of FIG. 3 (SEQ ID NO: 29). A Primer II is constructed so that its 3' end is complementary to the C-terminal portion of the globin gene coding sequence, up to and excluding the stop codon; it is further complementary to the gene encoding the linker and the predetermined peptide of interest. There is also provided a stop codon and the 5' portion of Primer II contains a unique restriction site. An example of Primer II is α-endo1 of FIG. 3 (SEQ ID NO: 24), which contains a Bgl II site. A Primer III is constructed so that its 5' portion contains the same restriction site as present in Primer II and has a 3' portion complementary to the antisense strand of the gene immediately 3' of the stop codon, e.g., AMKC1 of FIG. 3 (SEQ ID NO: 25). A Primer IV an be selected from a portion of the plasmid cloning vector into which the globin gene has been placed, which encompasses a unique restriction site and is complementary to the strand of the coding sequence of the globin gene, e.g., primer SP6 of FIG. 3 (SEQ ID NO: 26). Primers oriented relative to the globin gene as are Primers I and III will be referred to hereinafter as "sense" primers, primers in the opposite orientation such as Primers II and IV are "antisense" primers.

In this strategy, which has been used, for example, to construct an α-globin-α-endorphin fusion, Primers I and II and Primers III and IV are used to amplify a globin gene inserted in a cloning vector by polymerase chain reaction. The cloning vector containing the globin is then digested with the restriction enzymes appropriate for the sites of Primers I and IV and a three fragment ligation is performed in which the PCR amplified fragments are ligated to each other by the common restriction site of Primers II and III and are ligated to the cloning vector by the restriction sites of Primers I and IV. The gene encoding the globin-linker-peptide fusion protein can then be inserted into an expression vector.

Figure 2B:
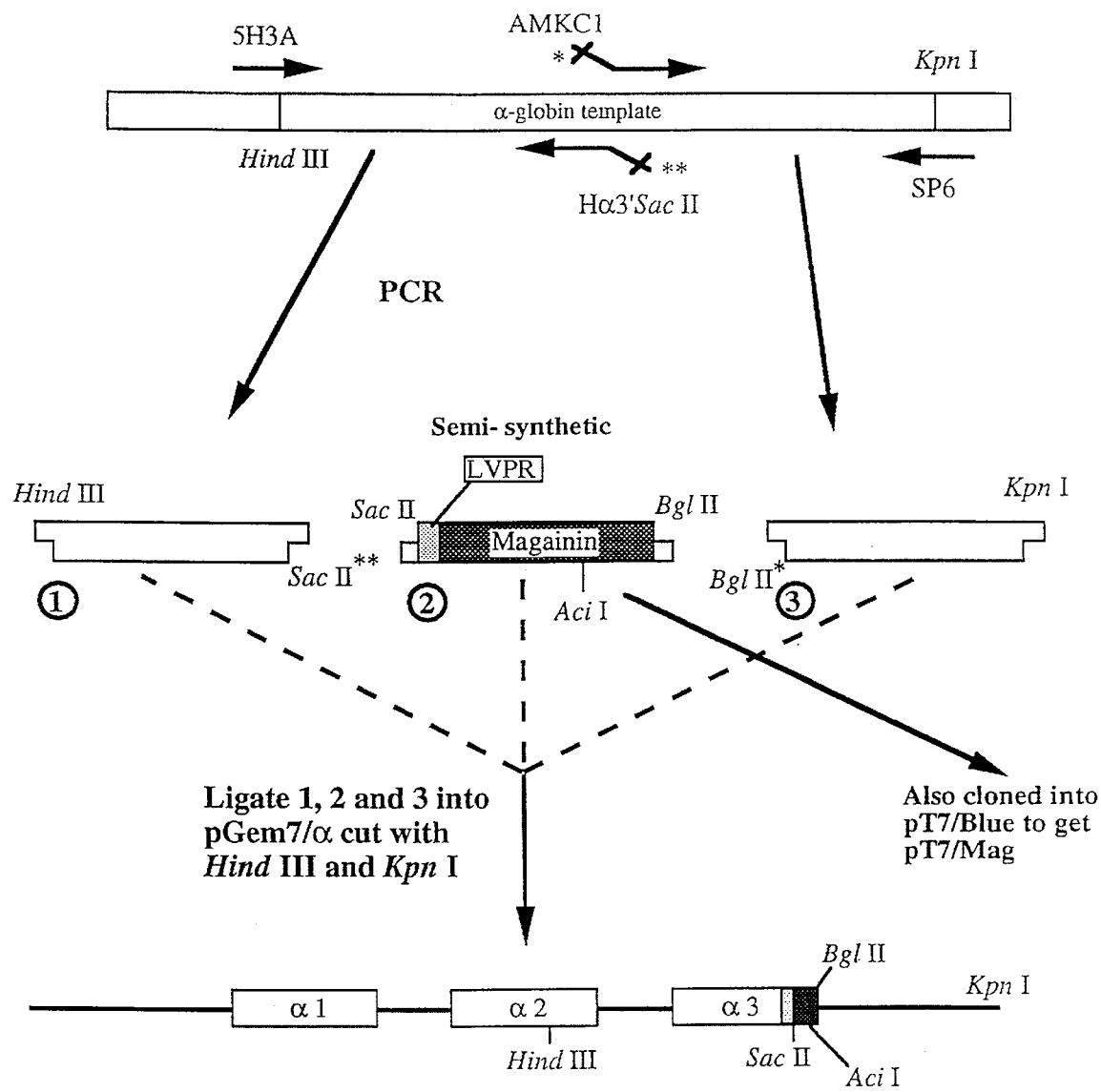
Figure 2D:
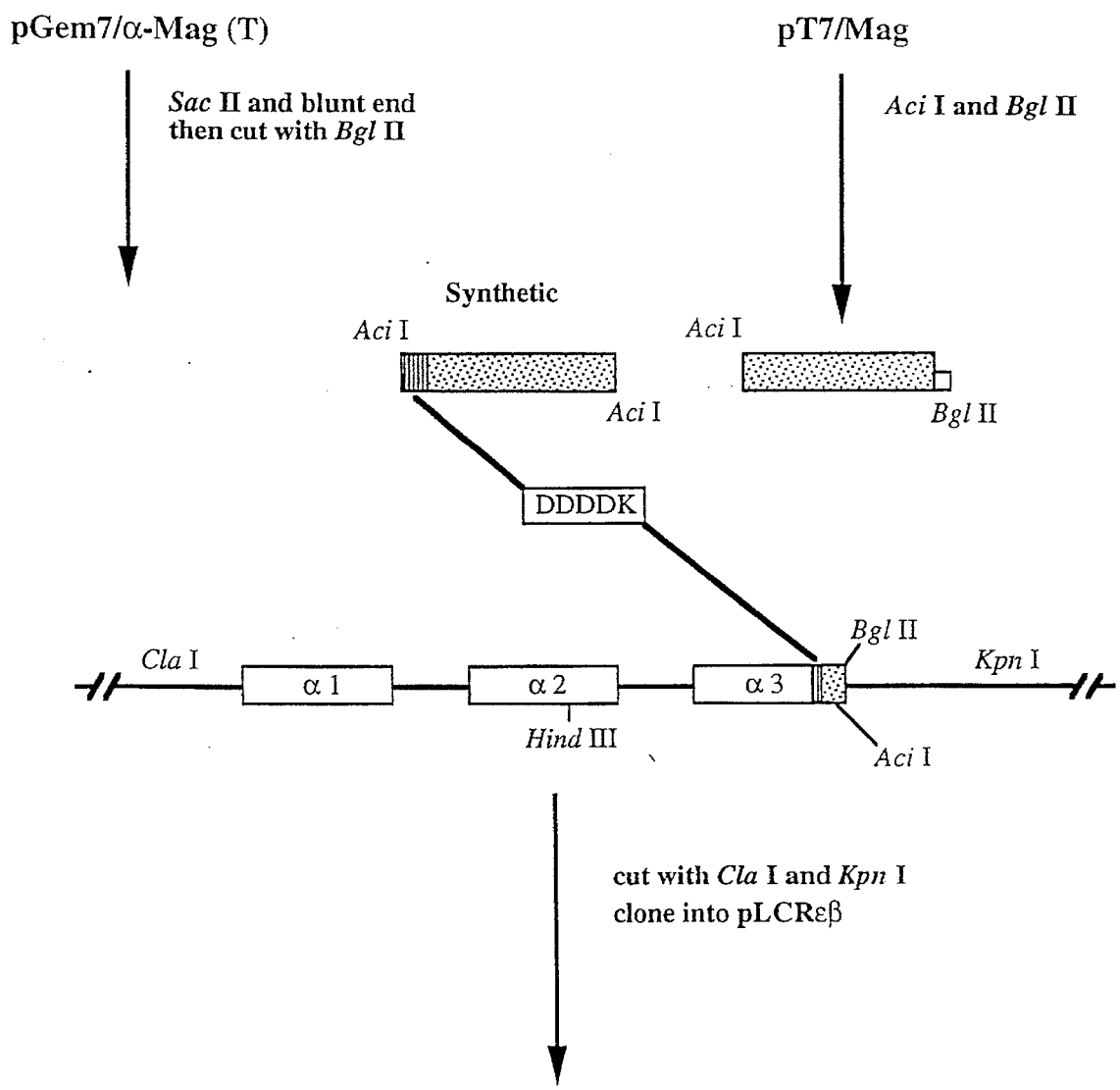

A first alternative strategy, which is schematically illustrated in FIG. 2B, is the preferred mode of construction when the desired peptide is longer than about 20 amino acids. Paired sense and antisense primers, I and II, and III and IV are used to amplify the contiguous portions of a 3' globin gene coding sequence, including the C-terminus, excluding the stop codon and of the 3' untranslated region. The 5' portions of primers II and III each contain, different arbitrarily chosen, unique restriction sites. For example, Hα3'-Sac II (SEQ ID NO: 27) and AMKC1-Bgl II (SEQ ID NO: 25) of FIG. 3. A double stranded insert is synthesized having at its 5' terminus the restriction site of primer II and at its 3' terminus the restriction site of primer III. The insert is then ligated between the coding fragment amplified with Primers I and II and the 3' untranslated fragment amplified with Primers III and IV. In a preferred embodiment the insert is constructed by means of the solid phase synthesis of one strand and of a complementary primer. The remainder of the complementary strand is synthesized enzymatically.

In a second alternative strategy of the invention, the gene encoding the fusion protein can be constructed from another fusion protein intermediary as is illustrated in the schematic of FIG. 2C. By way of illustration a gene encoding a β-globin/α-endorphin fusion protein was constructed from the corresponding α-globin fusion protein and a cloned β-globin gene. A fragment of the gene encoding the α-globin fusion protein is amplified using a 5' primer having a 5' restriction site, e.g. pep D4-Nde I (SEQ ID NO: 31), and the primer corresponding to Primer III in the scheme illustrated in FIG. 2A, e.g. AMKC1-Bgl II (SEQ ID NO: 25). The contiguous portions of the exon and 3' untranslated region were amplified with appropriate primers as above. The 3'-untranslated α-globin sequence was removed from the fragment encoding the peptide of interest and the remainder was ligated between the amplified β-globin coding region fragment and the amplified 3'-untranslated fragment of β-globin.

5.2 CONSTRUCTION OF EXPRESSION VECTORS

An expression vector of the present invention has an origin of replication suitable for replication/amplification of the vector in a transformable bacteria or its equivalent, which can be, for example, DH5α or HB101. The vector must also contain a locus that causes the gene encoding the fusion protein to be expressed at high levels specifically in erythropoietic cells. Such a locus control region (LCR) can consist of some or all of the super-hypersensitive sites found 5' and 3' of globin genes in mammalian species.

The structures of many LCRs of β-globin genes have been published, e.g., human, Li, Q., et al., 1985, J. Biol. Chem. 260: 14,901; Li. Q., et al., 1990, PROC. NATL.ACAD.SCI. 87: 8207; mouse, Shehee, W. R., et al., 1989, J.MOL.BIOL. 205: 41; rabbit, Margot, J. B., et al., 1989, J.MOL.BIOL. 205: 15; and goat, Li, Q., et al., 1991, GENOMICS 9: 488, each of which are incorporated by reference herein. The structure of the pig LCR is reported in a co-assigned U.S. patent application, Logan et al., U.S. patent application Ser. No. 08/105,989, filed Aug. 11, 1993, which is hereby incorporated by reference.

A shortened LCR has been constructed that contains only the DNase super-hypersensitive regions of the human β-globin locus control region (hereinafter "μβLCR"). This 6.5 kb LCR consists of four fragments of between 1.1 kb and 2.1 kb, and has been shown to be active in an orientation independent manner in transfected mouse erythroleukemia cells. The detailed structure of the μβLCR is provided in Grosveld, F. G., 1989, WO 89/01517 and 1992, WO 92/11380 which are hereby incorporated by reference in its entirety.

The structures of globins of many species have been reported. See, e.g., Hardison, R. and Miller, W., 1993, Mol. Biol. Evol. 10: 73–107.

5.3 PRODUCTION OF TRANSGENIC ANIMALS

Animals of any species, including but not limited to mice, rats, rabbits, guinea pigs, pigs, micro-pigs, and non-human primates, e.g., baboons, squirrel monkeys and chimpanzees can be used to generate the transgenic animals of the invention so long as a known globin LCR is functional in that species. The preferred embodiments employ mice and pigs. Any technique known in the art can be used to introduce the transgene into animals to produce the founder lines of transgenic animals. Such techniques include, but are not limited to pronuclear microinjection (Gordon et al., 1980, PROC. NATL. ACAD. SCI. USA 77: 7380–7384; Gordon & Ruddle, 1981, SCIENCE 214: 1244–1246; U.S. Pat. No. 4,873,191 (Oct. 10, 1989) T. E. Wagner and P. C. Hoppe); retrovirus mediated gene transfer into germ lines (Van der Putten et al., 1985, PROC. NATL. ACAD. SCI. USA 82: 6148–6152); gene targeting in embryonic stem cells (Thompson et al., 1989, CELL 56: 313–321); electropotation of embryos (Lo, 1983, MoL. CELL. BIOL. 3: 1803–1814); and sperm-mediated gene transfer (Lavitrano et al., 1989, CELL 57: 717–723); etc. For a review of such techniques, see Gordon, 1989, Transgenic Animals, INTL. REV. CYTOL. 115: 171–229, which is incorporated by reference herein in its entirety). Once the founder animals are produced, they can be bred, inbred, crossbred or outbred to produce colonies for the production of peptides according to the present invention.

The present invention provides for transgenic animals that carry the transgene in all their cells, as well as animals which carry the transgene in some, but not all cells, i.e., mosaic animals. The transgene can be integrated as a single transgene or in tandem, e.g., head to head tandems, or head to tail or tail to tail.

5.4 EXPRESSION, RECOVERY OF THE FUSION PROTEIN AND PURIFICATION OF THE PEPTIDE

5.4.1 Experesion In Vitro

A model system for the developmentally regulated expression of globin gene is found in the murine erythroleukemia cell line (C88 MEL) wherein erythroid differentiation is induced by low levels of dimethylsulfoxide (DMSO). Diessenroth, A. and Hendrick, D., 1978, CELL 15: 55; Wright, S., et al., 1983, NATURE 305: 333. Subsequently others have shown that when a foreign gene is introduced into C88 MEL under control of a β-globin LCR, its expression is also developmentally controlled by the same stimulus. van Assendelft, G. B., et al., 1989, CELL 56: 969. Differentiation of MEL C88 cells induced by DMSO results in the cessation of proliferation and the synthesis of tetrameric hemoglobin in high concentrations. The MEL C88 cell line thus provides an accurate in vitro model of erythropoiesis.

5.4.2 Recovery of Peptides From Transgenic Animals

To produce a peptide according to the present invention, a transgenic animal making the fusion globin of interest is bled into an anti-coagulant (EDTA or heparin) containing vessel. In one embodiment the red cell fraction of blood is isolated, by sedimentation at unit gravity, from the plasma, washed and then lysed by the addition of about 10 volumes of hypotonic buffer at physiologic pH, e.g., 10 mM Tris/PO$_4$ or the equivalent. In an alternative embodiment, the red cells can be lysed without prior sedimentation.

After lysis, the hemoglobins are subjected to the protease appropriate for the particular linker employed in the application. The reaction can be monitored by isoelectric focusing of the hemoglobins, by molecular sizing gel electrophoresis (SDS-PAGE) to detect the consumption of the fusion globin by the protease or by HPLC to detect the presence of the free peptide.

After the linker has been cleaved the predetermined peptide of interest can be separated from the globin fraction by any chromatographic or other physical technique, the choice of which will be dictated by the physico-chemical properties of the predetermined peptide of interest. Techniques include by way of example and not limitation: ion-exchange chromatography, RP-HPLC, gel-filtration chromatography, partition between organic and aqueous solvents, molecular filtration or dialysis with a molecular weight cut-off filter or dialysis membrane, crystallization and filtration of the hemoglobin with high salt and, lastly, the peptide of interest can be purified by specific binding to an antibody or other adsorbent such as the use of a nickel binding hexahistidine sequence. Alternatively, the intrinsic properties of the desired peptide can be used to purify the peptide. A peptide that is an enzyme inhibitor can be purified by affinity chromatography using the enzyme.

In a preferred embodiment of the invention the transgenic animal is a swine. The advantages of swine are their large size, early sexual maturity (about 6–7 months) and fecundity. A 6 month old animal will typically have a blood volume of about 6–8 liters containing a kilogram of hemoglobin. The animal can be bled at 4–6 week intervals in amounts of 1–2 liters at each bleeding, and can also be exsanguinated at sacrifice.

6. EXAMPLES

6.1 MATERIALS AND METHODS

6.1.1 Construction of Genes Encoding Fusion Proteins

6.1.1.1 α-Globin-DDDK-α-Edorphin

The α-endorphin/α-globin fusion gene was prepared as follows: A 96 nucleotide (nt) antisense oligomer (α-endo1-Bgl II, FIG. 3), (SEQ ID NO: 24) encoding the last four amino acids of α-globin, the cleavage sequence of enterokinase (AspAspAspLys) (SEQ ID NO: 19), and the 16 amino acids of α-endorphin (SEQ ID NO: 3), followed by a translation termination codon and a Bgl II restriction enzyme site was synthesized. A second primer, 5H3A-Hind III (SEQ ID NO: 23), a 30 nt oligomer encoding a portion of the 2nd exon of human α-globin gene overlapping a Hind III site was also synthesized. Using these two primers, PCR amplification was performed with human α-globin gene as the template. A 450 bp fragment containing part of the α-globin gene fused to the enterokinase cleavage site and α endorphin was obtained and cloned into pT7-Blue vector (Pharmingen, Calif.) to obtain pEndo2. This plasmid was sequenced to verify the integrity of the PCR amplified insert. A 600 bp fragment starting immediately after the stop codon of α-globin gene and containing the poly A signal and downstream sequences was also obtained by PCR amplification using a 5' primer AMKC1-Bgl II (SEQ ID NO: 25), and 3' primer SP6 (SEQ ID NO: 26), containing flanking Bgl II and Kpn I sites. This 600 bp fragment was cloned 3' to the α-endorphin containing sequences in Bgl II/Kpn I digested pEndo2. The resulting plasmid (pEndo2/α3') was digested with Hind III and Kpn I to obtain a ~1 kbp fragment which was ligated with ~1.7 kbp Cla I/Hind III segment of the human α globin gene. This segment contains 5' portion of the human α globin gene including the promoter. The resultant modified α gene (α*) was introduced into Cla I/Kpn I digested pLCReβ to get pLCRα*eβ. See FIG. 1. A 16.5 kbp DNA fragment for microinjection was obtained by digesting pLCRα*eβ with Sst II and Mlu I followed by electrophoresis and gel purification.

6.1.1.2 β-Globin-MD$_4$K-α-Endorphin

This fusion gens was constructed as follows: A portion of the human β-globin gens was amplified by PCR using primers 2β5-Bam HI (SEQ ID NO: 29) and β3-Nde I (SEQ ID NO: 30). A 1200 bp fragment was obtained and cloned into plasmid T7 blue to obtain p2H. This achieved the creation of an Nde I cloning site and the addition of an extra Methionine. A 600 bp fragment starting immediately after the last amino acid of α globin gens in pEndo2/α3' (see 6.1.1.1) and containing the downstream sequences including α-endorphin (SEQ ID NO: 3) was obtained by PCR amplification using primers pepD4-Nde I (SEQ ID NO: 31) and 3' primer AMKC1 (SEQ ID NO: 25). This fragment was digested with Nde I and cloned into p2H also digested with Nde I. The resulting plasmid p2HB was digested with Bam HI and another 2 Kbp fragment of the 5' end of the human β globin was cloned into it. The resultant plasmid pH2B2 was digested with Kpn I and Bgl II to obtain a 5.0 Kbp modified β globin gene fragment which was subcloned into pGEM7Z(+) to obtain pGEM 7.2HB2 (α3'). A 2.0 Kbp fragment of β globin gene starting after the stop codon and containing the 3' UTR poly A signal and was cloned by PCR using primers β3UTR (SEQ ID NO: 32) and an SP6 primer (SEQ ID NO: 26). This fragment was subcloned into pT7 blue and excised as an Sst I/Mlu I fragment. This fragment was then cloned into pGEM7/2HB2 digested with Sst I and Mlu I. This plasmid pGEM/β-globin α-endorphin (β*) was digested with Kpn I and Mlu I to derive the fusion gene which was cloned into pLCRαε to obtain pLCR αεβ*. For pronuclear microinjection, a linear fragment was obtained by digestion with SSt I and Mlu I.

6.1.1.3 α-Globin-D$_4$K-Magainin

Step 1: Magainin-α globin fusion containing an LVPR (thrombin) cleavage site was created as follows: Primers 5H3A-Hind III (SEQ ID NO: 23) and Hα3' Sac II (SEQ ID NO: 27) were used to PCR amplify a portion of the human α globin gene. A Sac II/Bgl II fragment containing magainin α coding sequences and thrombin cleavage signal was chemically synthesized (SEQ ID NO: 28). A third Bgl II/Kpn II fragment containing the 3' end of α globin gene starting immediately downstream of the stop codon was obtained by PCR using primers AMKC1 (SEQ ID NO: 25) and Sp6 (SEQ ID NO: 26). These three fragments were ligated into pGEM7/Huα (containing the promoter and the 5' portion of the human α globin gene) digested with Hind III and Kpn I. The resulting plasmid was designated pGEM7/α Mag (T).

Step 2: The thrombin site was replaced with an enterokinase (D$_4$K) site as follows: pGEM7/α Mag (T) was digested with Sac II, blunt ended and digested with Bgl II. A synthetic DNA fragment containing a portion of magainin, the enterokinase site and flanking Aci I sites was chemically synthesized. An Aci I/Bgl II fragment of the plasmid pGEM7/α Mag (T) containing the rest of the magainin coding sequence was isolated. The three fragments described above were ligated together to obtain pGEM7/α-Mag(EK). A Cla I/Kpn I fragment from this plasmid containing the modified α globin gene was cloned into pLCReβ to obtain pLCRαeβ, from which an Sst II fragment was isolated for pronuclear microinjection.

6.1.2 Production Of Transgenic Mice

All mice were obtained from the Jackson Laboratory, Bar Harbor, Me. and Taconic Laboratories, Germantown, N.Y. Transgenic mice were produced by pronuclear microinjection (Gordon et al., 1980, PROC. NATL. ACAD. SCI. USA 77: 7380–7384; Gordon & Ruddle, 1983, METHODS IN ENZYMOL. Recombinant DNA, Part C. 101: 411–433) of C57SJLF1×C57SJLF1 embryos, and founders were identified by IEF screening of hemoglobin.

DNA was injected into male pronuclei of fertilized mouse oocytes as described previously (U.S. Pat. No. 4,873,191 (Oct. 10, 1989), T. E. Wagner & P. C. Hoppe) Transgenic mice were identified by isoelectric focusing analysis of hemoglobin present in the red blood cells. Hemolysates of mouse blood were prepared and isoelectric focusing was performed in gels containing ampholytes in the pH6-8 range, following manufacturer's (IsoLab, Akron, Ohio) instructions. Human and mouse blood lysates were run as controls. The gels were fixed in 10% TCA, photographed and quantitated by laser densitometry.

6.1.3 RP-HPLC Analysis

Red blood cell lysates were prepared by osmotic lysis and centrifugation (Riggs, A., 1981, METH. ENZYMOL. 76: 5). The globin chains were separated from 150 µg of total hemoglobin by reversed phase HPLC (RP-HPLC) on a Dynamax 5 µm particle-size, 300A C4 (4.6×250 mm) column. Globin chains were eluted with a gradient of 37–48% (V/V) acetonitrile in 0.1% trifluoroacetic acid. The eluted proteins were monitored spectrophotometrically at 210 nm.

6.1.4 Enterokinase Cleavage

"Fusion" Hemoglobins were purified by elution from isoelectric focusing gels. Gel fragment containing the desired proteins were eluted by diffusion into enterokinase buffer (10 mM Tris. HCl, pH 8.0, 10 mM $CaCl_2$). Enterokinase (Sigma, St. Louis, Mo.) digestion was performed by adding 1.0 unit of enzyme per µg of protein in a final volume of 20 µl at 37° C. for 2 hours. The digested products were analyzed by SDS-PAGE and by Triton acid urea electrophoresis Alter, B. P. et al. 1980, BRIT. J. HEMAT. 44: 527.

6.2 Results

The results of the working examples of the present invention are summarized in Table 3 below.

TABLE 3

| Linker Seq. | Peptide Seq. | Globin | Charge Linker + Peptide | % Fusion Protein Expression |
|---|---|---|---|---|
| LVPR | Magainin | α | 6+ | None |
| NG | Magainin | α | 5+ | <1.0% |
| DDDDK | Magainin | α | 1+ | 1.6%, 6.2% |
| DDDK | Endorphin | α | −2 | 27.6% ± 14.4 |
| 2MD DDDDK | Endorphin | β | −4 | 12.2[1] |

[1]Note: individual transgenics having 20.0%, 20.1%, 5.5% and 2.6% were averaged. Three animals without detectable levels were also observed but excluded from the mean.

6.2.1 Endorphin

We created 6 transgenic mice by microinjection of a α-globin-α-endorphin Construct (#482) into fertilized mouse oocytes. Transgenic mice were initially identified by isoelectric focusing (IEF) analysis of their hemolysates. When compared with the IEF pattern of a hemolysate from a transgenic mouse expressing human Hemoglobin A, it was evident that 2 bands of different mobilities were present in the transgenic mice. In transgenic mice expressing unmodified human α and β genes, up to 6 different types of hemoglobins can be formed: either mouse αβ or mouse $α_2β$ plus mouse $α_2β$ (depending on one or two globin genes present in the mouse genome), human αβ, human α/mouse β, and one or two human β/mouse α hybrids. As shown in FIG. 4A, six different bands are seen in mice 4-2 and 5-2 whereas only 5 bands are present in 4-1 and 6-5. We determined the composition of each band by RP-HPLC using mouse and human hemoglobin controls. This analysis revealed that hemoglobins containing the fusion α globin protein were abundantly expressed in all six transgenic mice. Densitometric tracing of the fixed IEF gel showed that the highest expression was obtained in mouse 4-1, where 47% of the total hemoglobin was comprised of human fusion α/human β-globins and human fusion α/mouse β globins dimers. In the six founder mice, the average level of the fusion α-globin was 27.6% of total α-globin. See Table 2. The range was between 8% and 47%. Two of the founder transgenic mice were bred to non-transgenic mice. The resultant progeny included several mice that expressed the fusion hemoglobin at high levels (FIG. 4B). In the second generation transgenic mice, the α-globin- α-endorphin fusion protein was uniformly about 45% of total α globin, indicating that much of the variation in the first generation animals was due to mosaicism. This high level of expression of the modified human hemoglobin in founder as well as second generation transgenic mice indicates that the fusion of α endorphin to α globin does not destabilize the structure or function of the variant hemoglobin.

6.2.2 Magainin

The magainin peptide has a net charge at physiological pH of +4. Three different linker sequences were used to construct magainin α-globin fusion proteins: the thrombin sensitive sequence LVPR (Construct #516); the hydroxylamine sensitive sequence NG (Construct 561); and the enterokinase sensitive sequence DDDDK (Construct #560). As shown in Table 2, the net effects on the charge of the β-globin exerted by peptide and linker together were respectively +6, +5 and +1 respectively. Only the last of these examples was successfully incorporated into a substantial fraction of the circulating hemoglobin.

Two transgenic mice were created using the expression vector containing the DDDDK(SEQ ID NO: 19)-magainin fusion gene. IEF analysis revealed that both the human β globin and the fusion α globin were expressed, as evidenced by the presence of two inter-species hybrids (FIG. 4B). The human fusion hemoglobin (fusion α/β) was not apparent from this analysis. Most likely, this is due to the expected similar isoelectric points of the mouse and fusion human hemoglobins (the fusion protein is more basic than Hb A). The expression of the novel globin and its expected molecular size were confirmed by SDS-PAGE analysis (FIG. 4C). In the hemolysate prepared from transgenic mice expressing the magainin fusion hemoglobin, in addition to the expected~16 kD globin bands, a slower migrating novel band was also seen. This is likely to be the fusion α globin, which is expected to be larger than α globin by approximately 3 Kd. Both transgenic mice expressing magainin fusion were bred to non-transgenic mice and in each case the transgene was faithfully transmitted to the next generation. This indicates that the expression of the magainin fusion was not deleterious to the physiological function of the erythrocytes.

We tested the magainin fusion by enterokinase cleavage followed by RP-HPLC of the cleavage products. The magainin sequence does not contain any DK or EK sequences. The digested globin released a peptide that corresponded in elution with the synthetic magainin. No additional peptides were recovered. Similar digestion patterns were obtained when either the crude hemolysate or the IEF purified hemoglobin was used as a substrate. The released peptide was collected. The RP-HPLC elution profile of the recovered peptide was identical to that of the chemically synthesized magainin. These results validate the hemoglobin fusion approach for the production of peptides in transgenic animals.

6.2.3 Analysis of Molecular Structure of the Fusion Globins

We analyzed the globin chain composition of the hemoglobin contained in the hemolysates of transgenic mice expressing human Hb A or the two fusion proteins by RP-HPLC. In all three samples mouse α and β globin and the human β globin were detected. In the Hb A expressing mouse, the human α globin eluted at the expected position, with an elution time of 53.31 minutes. No peak corresponding to normal human α globin was found in the samples derived from mice expressing fusion α-globins. Instead, in these samples, peaks presumably corresponding to the modified α globins eluted at 49.16 minutes (endorphin fusion), and 51.86 minutes (magainin fusion). We isolated these two peaks by preparative RP-HPLC and determined their respective mass by electron spray mass spectrometry (MS). Both samples gave strong positive ion electrospray-MS spectra with a major series of possible multiply-charged ions. When deconvoluted, these data showed major components of molecular mass 17327.4 Da and 18162.1 Da in the endorphin and magainin fusion globins respectively. These values are within 2 Da of the calculated mass of the fusion α globins. These results show that the designed fusion protein is synthesized correctly in the erythrocytes.

Next, we isolated mRNA from blood samples obtained from transgenic mice and converted it to cDNA by reverse transcription. cDNA corresponding to the fusion message were by amplified by PCR and cloned in plasmids. Two independent clones each were sequenced from the endorphin and magainin mice. In all cases, we identified the expected additional segment at the 3' end of the globin coding sequence. The designed enterokinase cleavage signal and the peptide sequences were present intact as designed. This proved that the modified gene was faithfully transcribed and processed and suggests that the intended fused peptide is likely to be made. Collectively, these results indicate that the fusion expression strategy is successful, and that the novel globin can be purified by chromatography or electrophoresis.

6.2.4 Enterokinase Cleavage

This expression system relies on the ability to easily purify the fusion hemoglobin and to recover the peptide of interest by specific cleavage. We tested the feasibility of peptide recovery by enterokinase digestion of IEF purified fusion hemoglobin (mixture of human α*β and hybrid human α* mouse β hemoglobin dimers). Enterokinase is a highly specific endoprotease and no cleavage sites for this enzyme are present in human or mouse α and β globins Zito, R., et al., 1964, J. BIOL. CHEM. 239: 1884. The release of endorphin, therefore, depends upon the accessibility of the cleavage site in the native state. As shown in FIG. 6, the digestion of the fusion protein is rapid and is easily detected by SDS-PAGE by the change in the migration of the fusion α globin. Triton acid urea denaturing gel electrophoresis revealed that the unmodified β chain remained intact and the fusion α chain was specifically cleaved. The digested α globin had a different electrophoretic mobility compared to that of the native human α globin, because of the presence of the DDDK signal at the C terminus. Digestion was effective using either purified hemoglobin or a crude hemolysate.

7. DEPOSIT OF MICROORGANISMS

The following plasmids were deposited with the American Type Culture Collection (ATCC), 12301 Parklawn Drive, Rockville, Md. 20852 on May 23, 1994.

| plasmid | containing | Accession No. |
| --- | --- | --- |
| pSelectβ | β-globin | ATCC 75782 |
| pSelectα | α-globin | ATCC 75783 |
| pμβLCRαεβ | αεβ expression cassette w/LCR | ATCC 75784 |

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

We claim:

1. A hemoglobin comprising at least one fusion protein comprising a globin polypeptide and a predetermined peptide having less than about 65 amino acids, wherein the globin polypeptide is attached to the predetermined peptide through a selectively cleaveable peptide bond and wherein the net charge of the selectively cleaveable peptide bond and the predetermined protein is −4 to +5.

2. The hemoglobin of claim 1, wherein the attachment of the globin polypeptide to the predetermined peptide is through the carboxy-terminal of the globin polypeptide.

3. The hemoglobin of claim 2 which comprises two of said fusion protein.

4. The hemoglobin of claim 2, wherein the selectively cleaveable peptide bond is a portion of a linker.

5. The hemoglobin of claim 4, wherein the linker is tetraaspartyl-lysine (SEQ. ID NO: 19), leucylvalylprolylarginine (SEQ. ID NO: 21), or isoleucylglutamylglycylarginine (SEQ. ID NO: 20).

6. The hemoglobin of claim 4, wherein the linker is asparaginylglycine or methionine.

7. The hemoglobin of claim 4, wherein the predetermined peptide is magainin.

8. The hemoglobin of claim 4, wherein the predetermined peptide is hirudin.

9. The hemoglobin of claim 4, wherein the predetermined peptide is an endorphin, a dynorphin, calcitonin, or oxytocin.

10. The hemoglobin of claim 4, wherein the α-globin is human, mouse, rabbit, goat, or porcine.

11. The hemoglobin of claim 4, wherein the β-globin is human, mouse, rabbit, goat, or porcine.

* * * * *